Figure 1:
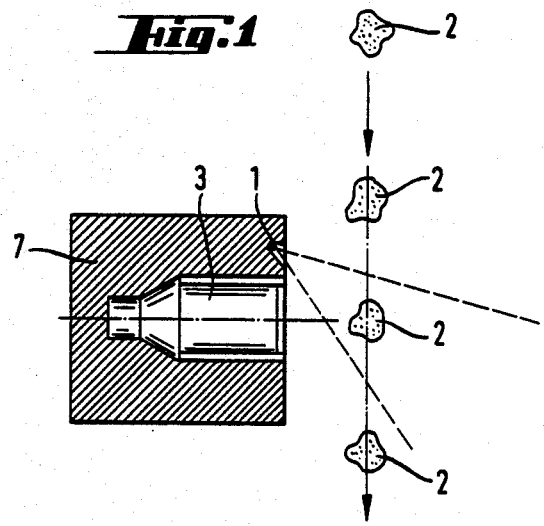

United States Patent [19]

Sipilä et al.

[11] Patent Number: 4,653,081

[45] Date of Patent: Mar. 24, 1987

[54] METHOD FOR TAKING THE RADIATION BACKGROUND INTO ACCOUNT IN THE DETERMINATION OF RADIATION INTENSITIES OF ANALYZED SAMPLES

[75] Inventors: Heikki J. Sipilä, Espoo; Kai J. Laamanen, Helsinki, both of Finland

[73] Assignee: Outokumpu Oy, Helsinki, Finland

[21] Appl. No.: 590,720

[22] Filed: Mar. 19, 1984

[30] Foreign Application Priority Data

Mar. 23, 1983 [FI] Finland ................................ 830968

[51] Int. Cl.$^4$ .................... G01N 23/223; G01F 23/00; B07C 5/00
[52] U.S. Cl. .................................. 378/45; 250/359.1; 209/576; 209/589; 378/49
[58] Field of Search ....................... 378/45, 53, 48, 49; 209/576, 589; 250/358.1, 359.1, 262

[56] References Cited

U.S. PATENT DOCUMENTS 3,404,275 10/1968 Martinelli .............................. 378/46
3,655,964 4/1972 Slight .................................... 209/589
4,121,098 10/1978 Jagoutz et al. ........................ 378/49

FOREIGN PATENT DOCUMENTS 0030894 7/1979 Japan .................................... 378/45
0179731 11/1982 Japan .................................... 378/53
2083618 3/1982 United Kingdom ................. 378/45

OTHER PUBLICATIONS

Bertin, Eugene, "Standardization with Scattered X-rays", *Intro. to X-ray Spectrometric Analysis*, pp. 344-348, 224-226, ©1978.

Primary Examiner—Craig E. Church
Assistant Examiner—Charles F. Wieland
Attorney, Agent, or Firm—Brooks Haidt Haffner & Delahunty

[57] ABSTRACT

According to the method of the invention, samples undergoing analysis for sorting are irradiated one by one in order to excite X-ray fluorescence. In order to take into account the background radiation, the quality whereof varies according to the frequency of the excited radiation, the radiation peak intensity $I_1$ is measured, as well as the respective intensity $I_2$ is measured at the same point of the radiation spectrum but in an essentially wider frequency range than the radiation peak. On the basis of the measured intensities $I_1$ and $I_2$ are defined the intensities of the X-ray fluorescence $F$ and the background radiation $T$, and the ratio of these two is used as the selective criterion when sorting the analyzed samples.

5 Claims, 3 Drawing Figures

METHOD FOR TAKING THE RADIATION BACKGROUND INTO ACCOUNT IN THE DETERMINATION OF RADIATION INTENSITIES OF ANALYZED SAMPLES

The present invention relates to a method for taking the radiation background into account in the determination of radiation intensities of analysed samples, wherein the said samples, such as pieces of ore, are one by one irradiated by at least one radiation source in order to analyse them for sorting, so that in order to eliminate the influence of radiation background, not only the radiation intensities are measured, but also the intensities of respective radiations at the same point of the radiation spectrum but in an essentially wider wavelength range, and that the intensities of radiation and background radiation are defined on the basis of the measured intensities, whereafter the ratio of the radiation intensity to the background radiation intensity is employed as the selective criterion when sorting the samples.

In the method according to the U.S. Pat. No. 3,404,275, pieces of ore are analysed by means of gamma radiation so that the intensities of the fluorescence K-line and the backscattered Compton radiation are determined. The ratio of the measured intensities is directly applied for defining the content of heavy elements in the irradiated pieces, and particularly the content of heavy elements located at the surface of the pieces. However, in the determination of the intensity of the backscattered Compton radiation, the form of the radiation peak created by the sample is not taken into account, in which case the quantity of background radiation varies as a function of the wavelength and the sample.

The purpose of the present invention is to achieve a method which is both more reliable and more secure in operation than the prior art methods. In the method of the present invention, the fluctuation of the background radiation caused by the primary radiation source, as a function of the wavelength, is taken into account when determining radiation intensities created in the analysis of pieces of ore, particularly as regards Compton-scattered radiation. The essential characteristics of the invention are enlisted in the appended patent claim 1.

According to the method of the present invention, the pieces of sample material are irradiated one by one at least by one gamma radiation source, in order to analyse the samples for sorting. The energy of the radiation source is chosen so that X-ray fluorescence is excited in the piece under analysis. According to the invention, the Compton-scattered background radiation is determined essentially at the X-ray fluorescence peak caused by the excitation source by means of employing in the detector two channels for the same excitation source, so that one channel is used for measuring the intensities of the X-ray fluorescence and the Compton-scattered background radiation, whereas the other channel is used for measuring the intensities of both radiations in an essentially wider frequency range of both sides of the X-ray fluorescence peak. On the basis of the obtained readings it is possible to mathematically determine the X-ray fluorescence and the respective Compton-scattered background radiation intensity. By forming a ratio of these mathematical quantities which are determined on the basis of the measured intensities, a quality ratio is obtained; this quality ratio describes the content of precious minerals at the surface of the sample piece. When the quality ratio exceeds the required treshold ratio, the analysed block is sorted as ore.

Figure 2:
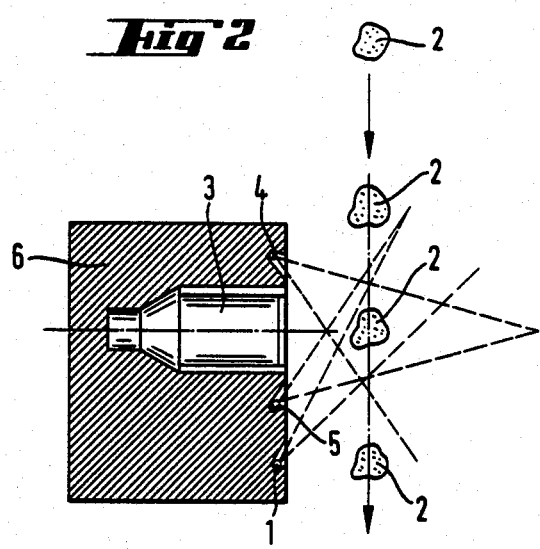

The mathematical operations for defining the quality ratio according to the invention, as well as the practical arrangement required for measuring the intensities in order to determine the quality ratio, are described below with reference to the appended drawings, where FIG. 1 is a schematical illustration of one preferred embodiment of the invention, and FIG. 2 is an illustration of the embodiment of FIG. 1 combined with the gamma scattering method of the FI Pat. No. 61 361.

Figure 3:
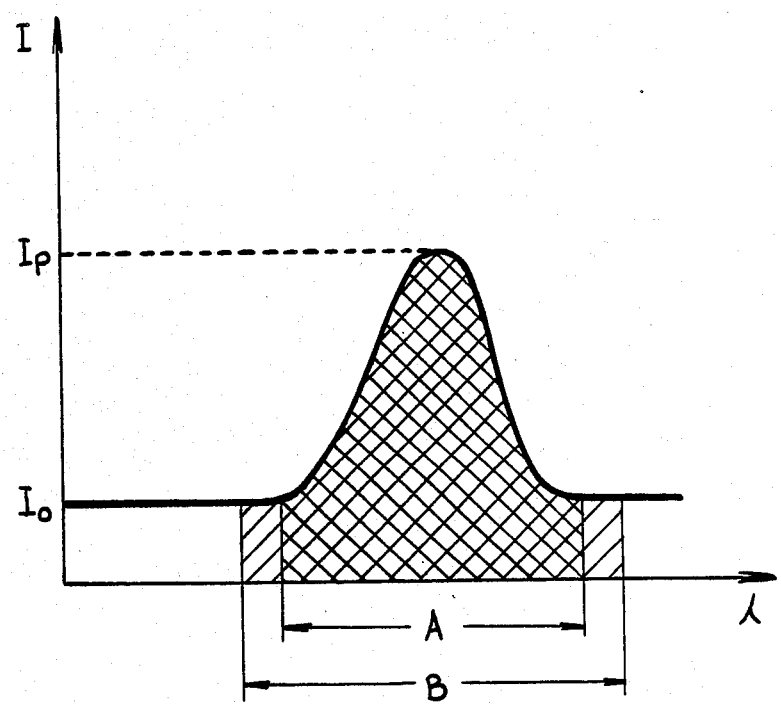

FIG. 3 illustrates the relationships between the variables T, kT, $I_1$ and $I_2$.

According to FIG. 1, the gamma radiation source 1 irradiates the piece 2; the Compton-scattered background radiation excited in the said piece is measured by means of the detector 3 placed within the radiation shield 7, the said detector being for instance an energy-dispersive scintillation detector. The detector 3 comprises two channels, one for measuring the intensity of the X-ray fluorescence F excited at the frequency of the X-ray fluorescence peak, as well as the intensity of the background radiation T, the major part whereof is Compton-scattered radiation. The other channel is employed for measuring the intensities of the X-ray fluorescence F and the background radiation in an essentially wider frequency range at both sides of the X-ray fluorescence peak. Hence the total intensities $I_1$ and $I_2$ obtained for the channels are:

$$I_1 = F + T \tag{1}$$

$$I_2 = F + kT \tag{2}$$

where k is a coefficient larger than 1, because the channel 2 measures the radiation in a wider area than the channel 1. When expression (2) is subtracted from expression (1), we obtain $$I_2 - I_1 = T(k-1) \tag{3}$$

Now the background radiation T is described by the expression $$T = \frac{I_2 - I_1}{k - 1}. \tag{4}$$

From expressions (1) and (2) we obtain the following expression for the X-ray fluorescence radiation F:

$$F = \frac{kI_1 - I_2}{k - 1}. \tag{5}$$

By forming a ratio of the expressions (5) and (4), the following expression is obtained for the quality ratio $T_o$ according to the method of the invention:

$$T_o = \frac{kI_1 - I_2}{I_2 - I_1}, \tag{6}$$

which describes the content of precious minerals at the surface of the analysed piece 2. On the basis of the quality ratio $T_o$ determined for the piece, the piece 2 is sorted either as ore or as dead rock depending on whether the quality ratio $T_o$ of the piece surpasses the predetermined sorting criterion or whether it remains below it.

The method of the invention can also be used in connection with prior art sorting and analysing methods, such as the gamma scattering method introduced in the FI Pat. No. 61 361. In that case, a suitable radiation source 1, applicable in the present invention, is placed near the radiation sources 4, 5 of the FI Pat. No. 61 361, preferably within the same radiation shield 6. When the method of the present invention is employed in connection with the method of the FI Pat. No. 61 361, the radiation source 1 is used for irradiating either only those pieces which are sorted as dead rock in the method of the FI Pat. No. 61 361, or preferably all pieces, in which case the quality ratio $T_o$ is applied for those samples which were sorted as dead rock in the method of the FI Pat. No. 61 361.

In the method of the present invention, the radiation source 1 is advantageously for instance Cs-137 or Ir-192 while the radiation source energy fluctuates between 300 and 660 keV. The radiation sources 4 and 5 of the FI Pat. No. 61 361 can be for example Am-241 and Cs-137, the intensities whereof are roughly 60 keV and 600 keV.

FIG. 3 illustrates the relationships between the variables T, kT, $I_1$ and $I_2$. The coordinate axes are wavelength $\lambda$ versus intensity I. The drawing shows one X-ray fluorescence peak P. The peak P is limited to the range of wave-lengths A. This peak includes the background radiation T over the range A. The total intensity of the peak is the sum of background radiation T plus X-ray fluorescence F. The total intensity of the peak P is measured by one channel of a detector over the range A. This total intensity is $I_1 = F + T$.

Another detector channel measures the total intensity across the wave-length range B, which is a wider range than range A. The total intensity measured by this channel is called $I_2$. The amount of X-ray fluorescence included in $I_2$ is the same as that in $I_1$.

Although certain preferred embodiments of the present invention are described in the specification above, it is naturally clear that the method of the invention can be applied in numerous other ways, too. Thus, when the method of the invention is combined to a prior art analysing method, the method of the present invention can, if so desired, also be used as the main criterion in the sorting of pieces. Moreover, when combined to a prior art method, the method of the present invention can be provided with a separate detector, or the same detector can be employed for both methods.

We claim:

1. A method for taking the radiation background into account in the determination of radiation intensities of samples undergoing analysis for sorting, comprising the steps of: irradiating samples under analysis by at least one radiation source in order to excite X-ray fluorescence, measuring a radiation intensity peak $I_1$, measuring radiation intensity $I_2$ at the same point as the intensity peak $I_1$, but in a wider frequency range than the intensity peak $I_1$, using the measured intensities $I_1$ and $I_2$ to define the respective intensities of the X-ray fluorescence F and the background radiation T, and then comparing the intensities F and T to determine the precious metal contents at the surface of the sample.

2. The method of claim 1, comprising choosing the ratio of the X-ray fluorescence F to the background radiation T as the quality ratio $T_o$, describing the sorting results.

3. The method of claim 2 or 1, wherein the detector comprises two channels, one for measuring the intensity $I_1$ and the other for measuring the intensity $I_2$.

4. The method of claim 2 or 1, comprising employing at least one energy-dispersive scintillation detector as the detector.

5. The method of claim 1, wherein the energy level of the radiation source is between 300 and 660 keV.

* * * * *